United States Patent [19]

Muñoz

[11] Patent Number: 5,470,000

[45] Date of Patent: Nov. 28, 1995

[54] SUPPORT, CARRIER BELT SYSTEM

[75] Inventor: Jose C. Muñoz, Pico Rivera, Calif.

[73] Assignee: McGuire Nicholas Company, Inc., Commerce, Calif.

[21] Appl. No.: 230,078

[22] Filed: Apr. 20, 1994

[51] Int. Cl.⁶ ..................................... A45F 5/00
[52] U.S. Cl. ..................... 224/224; 224/901; 224/904; 602/19; 2/300; 2/312; 2/319
[58] Field of Search ..................... 224/224–226, 224/252, 253, 901, 904, 151, 202; 2/300, 311, 312, 318–320; 128/96.1, 99.1, 100.1, 101.1, 845, 876; 602/19

[56] References Cited

U.S. PATENT DOCUMENTS

| | | | |
|---|---|---|---|
| 882,445 | 3/1908 | Basch | 2/318 |
| 1,478,497 | 12/1923 | Welch | 224/224 |
| 3,543,977 | 12/1970 | Lockridge | 224/901 X |
| 4,165,826 | 8/1979 | Chica | 224/901 X |
| 4,537,341 | 8/1985 | Kelly | 224/202 |
| 4,747,527 | 5/1988 | Trumpower | 224/224 |
| 4,819,846 | 4/1989 | Hannemann | 224/240 |
| 4,923,105 | 5/1990 | Snyder | 224/255 |
| 4,932,576 | 6/1990 | Ashley | 224/253 |
| 4,953,765 | 9/1990 | Little et al. | 224/151 |
| 4,957,231 | 9/1990 | Kalisher | 224/151 |
| 4,966,320 | 10/1990 | DeSantis et al. | 224/901 X |
| 4,986,459 | 1/1991 | Yarbrough, Jr. | 224/253 |
| 4,993,614 | 2/1991 | Bonofiglo | 224/253 |
| 5,009,347 | 4/1991 | Phelps | 224/901 X |
| 5,050,830 | 9/1991 | Hall | 224/901 X |
| 5,081,714 | 1/1992 | Liu | 2/2 |
| 5,122,111 | 6/1992 | Sebastian et al. | 602/19 |
| 5,147,261 | 9/1992 | Smith et al. | 482/106 |
| 5,148,549 | 9/1992 | Sydor | 2/312 X |
| 5,240,156 | 8/1993 | Sicotte et al. | 224/151 |
| 5,263,618 | 11/1993 | Talavera | 224/901 X |
| 5,337,933 | 8/1994 | Nunez | 224/151 |
| 5,349,706 | 9/1994 | Keer | 2/300 |
| 5,413,262 | 5/1995 | Dewire et al. | 224/253 |

Primary Examiner—J. Casimer Jagyna
Attorney, Agent, or Firm—Steven G. Roeder; Sheldon & Mak, Inc.

[57] ABSTRACT

A support, carrier belt system (7) is provided which includes a support belt (9) having two tightening straps (13), and a carrier device (9) which includes a tool-carrying compartment having a pocket or tool-carrying loops. A support belt (9) has a first fastener (14) at each end (15), in which the first fastener (14) is an interlocking system with a second fastener (19) which is at a free end (17) of the tightening straps (13). A carrier device (11) is attachable to both the first fastener (14) of the support belt (9) by the use of a third fastener (27) and a fourth fastener (31) to provide more secure hold by the support belt (9).

16 Claims, 4 Drawing Sheets

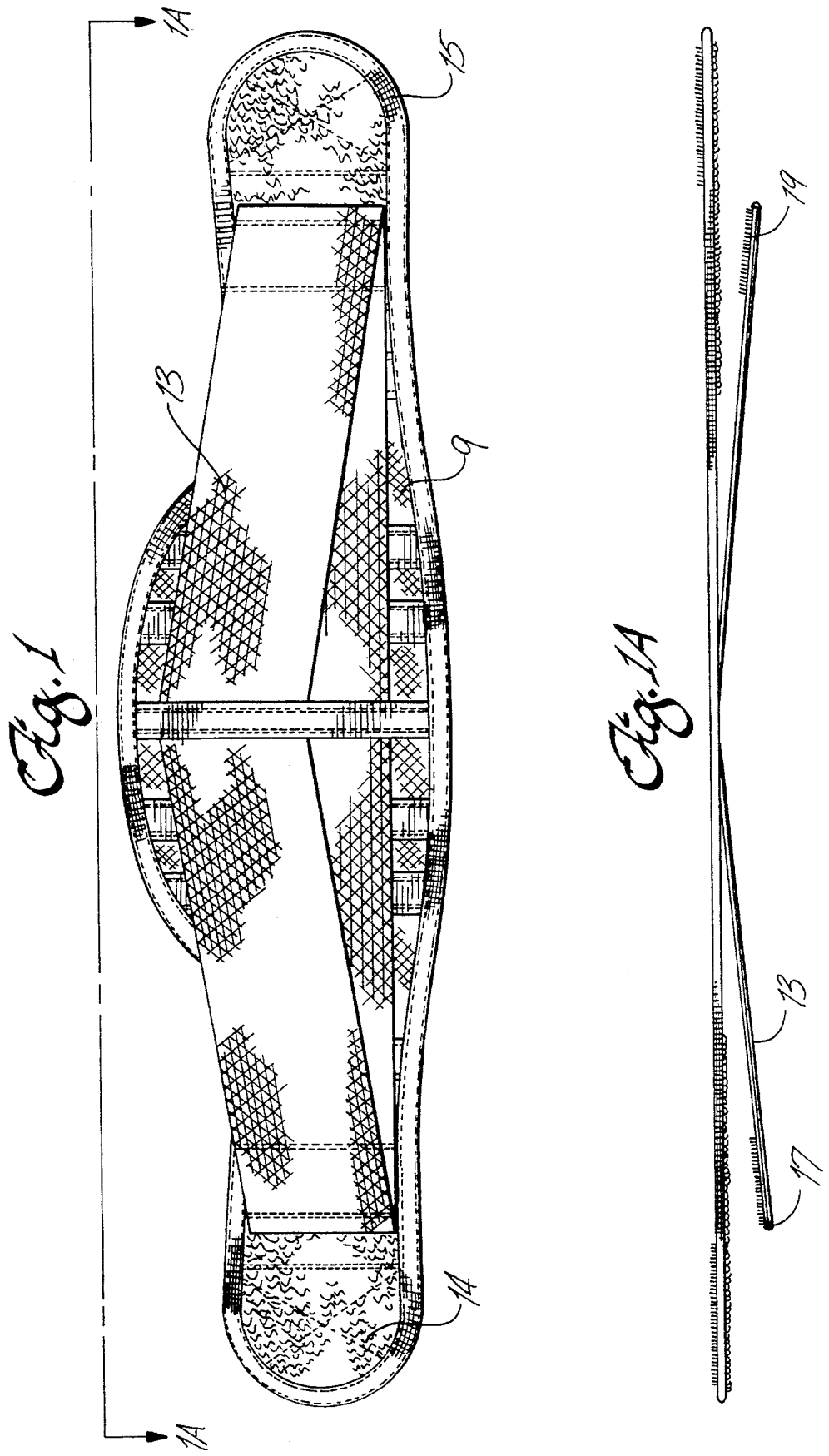

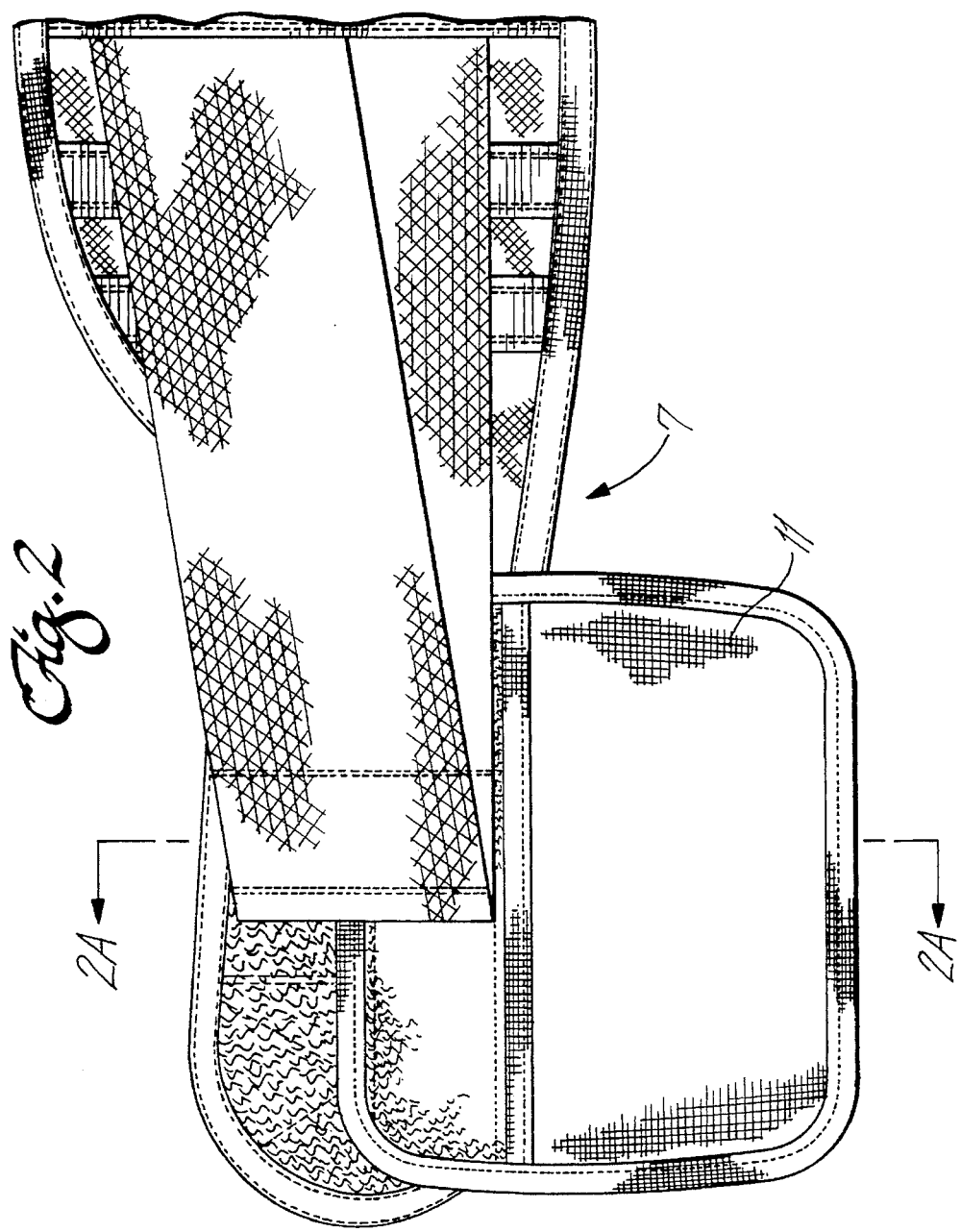

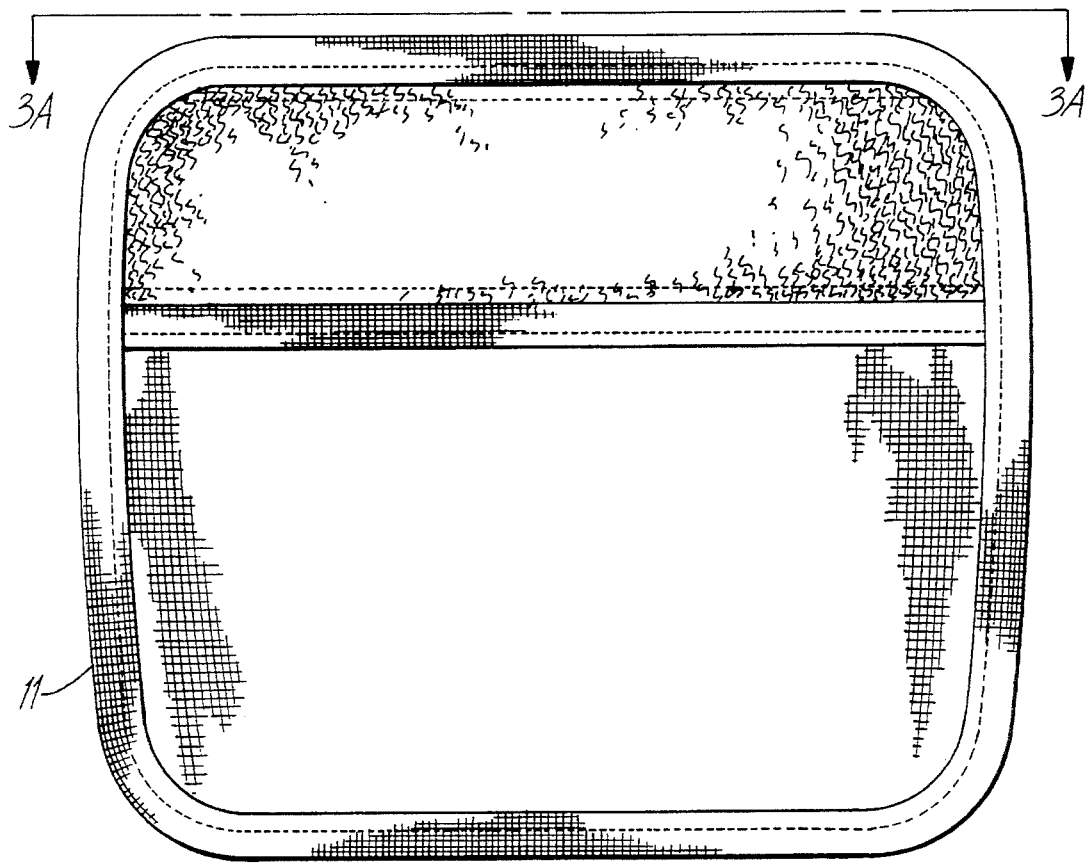
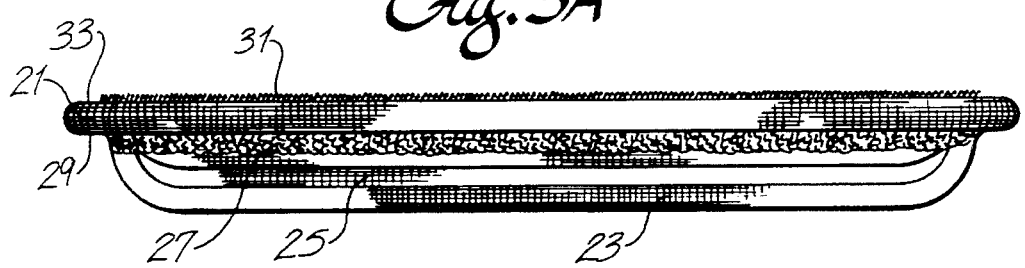

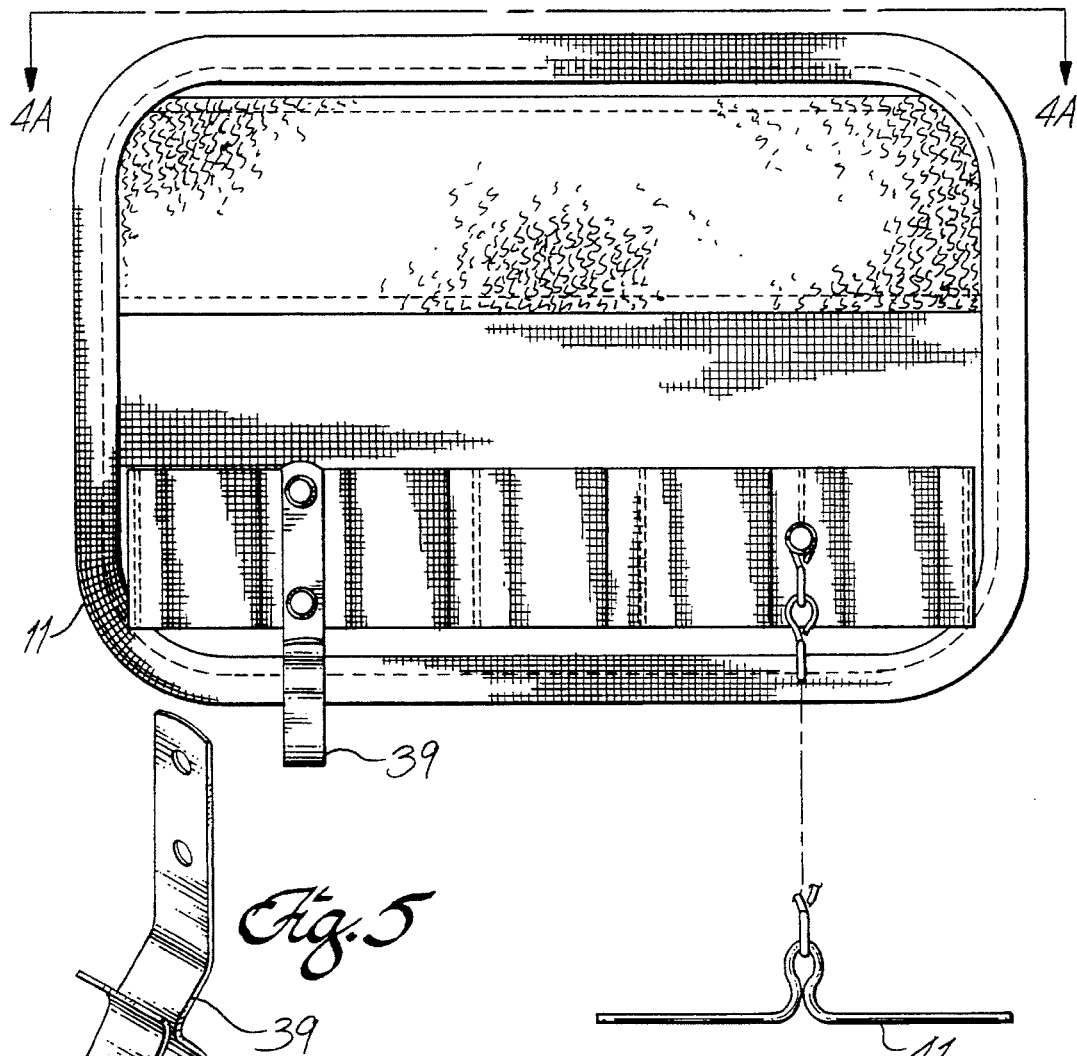
Fig.4
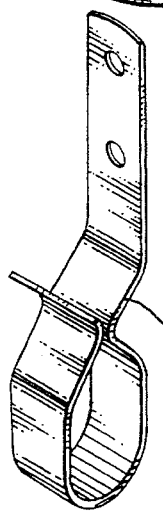
Fig.5
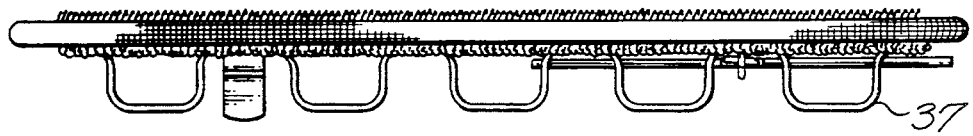
Fig.4A 5,470,000

SUPPORT, CARRIER BELT SYSTEM

BACKGROUND

This invention relates to support belts. Often people wear support belts to support their backs. The wearing of support belts is specially beneficial for people who lift, carry heavy items, or carry tools. Because they are engaged in their work, which requires them to carry one or more personal items, such as tools and other useful items, they sometimes use belt accessories which are designed to carry their belongings.

Prior art belt/accessory designs have a fastening device, such as a loop and hook-type attachment (frequently sold under the VELCRO trademark) only on one side. Because the fastening device is only on one side, the belt does not grip the accessory very effectively or very securely. Often an accessory, although it is attached to the belt, is loose and cannot hold much weight. Moreover, when the support belt is loosened to adjust the grip around the waist, the accessories are either detached or loosely held by the belt. Therefore, even a simple adjustment around the waist can be time consuming and requires both hands.

For the foregoing reasons, there is a need for a support belt system which incorporates an accessory design that is held by the support belt more securely and effectively.

SUMMARY

The present invention is directed to a support, carrier belt system that can carry personal items of the wearer effectively and securely.

The system comprises a support belt and at least one carrier device or accessory. The support belt has opposed end segments with fasteners on the end segments for adjustably connecting the end segments to each other. The support belt includes a pair of tightening straps, each tightening strap having one end attached to the belt and an opposed free end. Each tightening strap has on its free end a second fastener for adjustably connecting the tightening strap to a respective one of the first fasteners.

The carrier device comprises a body portion having a front face and rear face. The front face has a third fastener for removable connection to the second fasteners on the tightening strap, and the rear face has a fourth fastener for removable connection to the first fasteners on the belt end segments. Thus, the support device can be attached to one of the support belt end segments and one of the tightening straps, so that the support belt can be adjusted without disengaging the carrier device from the support belt. Preferably, the fasteners are loop-type and hook-type attachments.

In this specification, the terms "loop-type" and "hook-type" fasteners are intended to mean a releasable fastening device of the type having a mat composed of a carrier strip having secured to it a mass of looped fibers in which engage, in the attached positions, a multitude of hooked upstanding filaments carried by the pad. When engaged in the mat, the hook-shaped elements hold the pad in engagement with the mat, but excessive force can tear the two parts apart. One example of such a mat and pad arrangement is that sold under the proprietary tradename "VELCRO."

These accessories can be firmly secured onto the belt because they have fastening devices on both sides. Moreover, because these accessories are held very securely, weighty items can be carried by these accessories and the belt, and special tool-carrying compartments can be integrated into the carrier system.

These special tool-carrying compartments can be durably designed pockets or a series of loops to carry long and heavy tools, such as a wrench and a hammer. Moreover, specially designed tool holders to carry heavier or awkwardly shaped tools can be integrated into the system. Such specially designed tool holders can be a tool-holding clip or a tool-holding rod.

Another advantage of the invention is that the accessory remains attached to the belt while adjusting the belt (loosening or tightening the belt), so that the need to hold onto the accessory while the belt is being adjusted is reduced.

DRAWINGS

These and other features, aspects, and advantages of the present invention will become better understood with regard to the following description, appended claims, and accompanying drawings where:

FIG. 1 is a front view of a support belt with the present invention;

FIG. 1A is a top plan view of the support belt of FIG. 1 taken on line 1A—1A in FIG. 1;

FIG. 2 is a front view partially exploded of a belt system according to the present invention;

FIG. 2A is a vertical sectional view of the system of FIG. 2 taken on line 2A—2A in FIG. 2;

FIG. 3 is a front view of a carrier device with a cavity useful in the system of the present invention;

FIG. 3A is a top plan view of the carrier device of FIG. 3 taken on line 3A—3A in FIG. 3;

FIG. 4 is a front view of a second carrier device useful in the system of the present invention, with a plurality of loops, a tool-holding clip, and a tool-holding rod;

FIG. 4A is a top plan view of the carrier device of FIG. 4 taken on line 4A—4A in FIG. 4; and FIG. 5 is a perspective view of the tool-holding clip shown in FIG. 4.

DESCRIPTION

With reference to the figures, a support belt system 7 according to the present invention comprises a support belt 9 and at least one of a multitude of carrier devices 11.

FIG. 1 shows the support belt 9 with adjustable tightening straps 13. The support belt 9 has two end segments 15 with one or multiple fastening devices at each end. The preferred embodiment is a pair of the fastening devices, referred to as first fasteners 14, as shown in FIG. 1, with the use of a loop-type fastening device on the outer side, away from the user, and of a hook-type fastening device on the inner side, toward the user, of the support belt 9. The use of a pair of the fastening devices on each end is preferred because when a pair is used, then either end segment 15 of the support belt 9 can be toward the body of the wearer and the other end segment 15 can be on it. Also, a loop-type fastening device is preferred to be used on the outer side, away from the user, because the exterior surface of the loop-type fastening device is soft compared to the hook-type fastening device, and when a wearer inadvertently rubs his skin over the outer side, the skin is not irritated as much as it would be when the hook-type fastening device is on the outer side.

The tightening straps 13 are held securely at the middle portion of the support belt 9. The tightening straps 13 are made of flexible and stretchable material, and the preferred method to attach the tightening straps 13 onto the support belt 9 is by stitches at the middle portion of the support belt 9, but other means such as rivets or staples are also acceptable. A free end 17 of each tightening strap 13 has a second fastener 19, to be attachable to the outer side, away from the user, of the support belt 9. A loop-type or hook-type fastener is recommended for the second fastener 19, in accordance with the type of the fastener used as the first fastener 14.

Turning to FIG. 3, an example of a carrier device 11 according to the present invention is shown. The carrier device 11 has a body portion 21 and a pocket-forming cover 23. The body portion 21 and the pocket-forming cover 23 are securely sewn together along the edges of the pocket-forming cover 23. Not all edges of the pocket-forming cover 23 are to be completely sewn together, so the carrier device 11 has an opening 25, so a wearer of the carrier device 11 has access to the pocket which is formed by the body portion 21 and the pocket-forming cover 23. Personal items of the wearer can be inserted into the pocket to be carried by the carrier device 11.

A third fastener 27 is sewn on a front face 29 of the body portion 21, and a fourth fastener 31 is sewn on a rear face 33 of the body portion 21. These third fasteners 27 and fourth fasteners 31 primarily rely on removable and adjustable fasteners, such as hook-type fasteners and loop-type fasteners. The loop-hook relationship as shown is desirable, but reversal can be used. Also, it is preferable to wrap the edges of the body portion 21 and the pocket-forming portion 23 with edge protectors as 35. These edge protectors 35 are sewn over each edge the protector is to protect. Sewing is preferred for attaching the pocket-forming cover 23, the third fastener 27, the fourth fastener 31, and edge protectors 35 onto the body portion 21, but other forms of fastening can be used, such as stapling, riveting, and bonding.

A second carrier device 11 is shown in FIG. 4. This device 11 has one or more loops formed by a loop-forming material 37. The loop-forming material 37 can be formed to make a single loop or multiple loops as shown by the figure. A strip of loop-forming material 37 can be sewn into the body portion 21 at multiple places to form multiple loops. A personal item, such as a screwdriver, a wrench, or a hammer, of the wearer can be inserted into each of the loops to be carried on the carrier device.

An important feature of the invention is that the carrier device has fastening devices on both the front face 29 and the rear face 33. Because these fastening devices are on both the front face 29 and the rear face 33, the carrier device is held more securely, and as a consequence the carrier device can carry more weight. Because more weight can be carried by the support belt, a special tool-carrying holder, such as a tool-holding clip or a tool-holding rod, can be integrated into the carrier system.

These special tool-carrying holders can be designed to carry heavier or awkwardly shaped tools, and these tool holders can be a tool-holding clip 39 or a tool-holding rod 41. The tool-holding clip 39, as shown in FIG. 5, is specially designed to accept large tools with a ring or a hook, such as an electric drill with a ring for hanging. The tool-holding rod 41, as shown in FIG. 4, is specially designed to accept large tools with multiple-pronged hooks. These tool-carrying holder designs are not limited to the two devices shown in the drawing. The ideal attaching means for these tool holders are rivets to secure them onto the body portion 21, but other means are available such as sewing or stapling.

FIG. 2 shows a preferred use of the support belt 9 and the carrier device 11 in the support, carrier belt system 7. As shown in FIG. 2A, the carrier device 11 is held securely by both the third fastener 27 on its front face 29 and the fourth fastener 31 on its rear face 33. It is apparent from the preferred use shown in FIG. 5, that when the tightening strap 13 is detached to adjust the grip around the waist of the wearer, the carrier device 11 is still securely attached to either the support belt 9 or the tightening strap 13, thus eliminating the need to hold onto the carrier device during adjustments.

Although the present invention has been described in considerable detail with reference to certain preferred versions thereof, other versions are possible. For example, the tool-holding clip can be in a form of an alligator clip hung onto the body portion 21 of the carrier device 11 using a chain, similar to the attaching method used for the tool-holding rod 41. Therefore, the spirit and scope of the appended claims should not be limited to the descriptions of the preferred embodiment or the preferred versions contained therein.

What is claimed is:

1. A support, carrier belt system comprising:
   a) a support belt, comprising opposed end segments with first fasteners for adjustably connecting the segments to each other, the belt having a pair of tightening straps therein, each tightening strap having one end attached to the support belt and an opposed free end, each tightening strap having on its free end a second fastener for adjustably connecting the tightening strap to a respective one of the first fasteners; and
   b) at least one carrier device comprising a body portion having a front face and a rear face, the front face having a third fastener for removable connection to the second fasteners and the rear face having a fourth fastener for removable connection to the first fasteners so that the support device can be attached to one of the support belt end segments and one of the tightening straps so that the support belt can be adjusted without disengaging the carrier device from the support belt.

2. The system of claim 1, wherein the carrier device further comprises a pocket-forming cover having a plurality of edges, at least one of the edges being fastened to the body portion to form a cavity with an opening so that a personal article of the wearer of the belt can be inserted into the cavity.

3. The system of claim 1, wherein the carrier device further comprises a loop-forming material having two ends, each end of the loop-forming material being fastened to the body portion to form a loop so that a personal article of the wearer of the belt can be inserted into the loop, and thus carried by the carrier.

4. The system of claim 3, wherein the loop-forming material is fastened to the body portion at multiple locations to form a plurality of loops so that a personal article of the wearer of the belt can be inserted into each loop, and thus carried by the carrier.

5. The system of claim 1, wherein the carrier device further comprises a tool-holding clip attached to the body portion so that a personal article of the wearer of the belt can be held within the tool-holding clip, and thus carried by the carrier.

6. The system of claim 1, wherein the carrier device further comprises a tool-holding rod attached to the body portion so that a personal article of the wearer of the belt can be carried by the tool-holding rod, and thus carried by the carrier.

7. The system of claim 1, wherein the first fastener is comprised of a hook-type fastener on the inner side, and a loop-type fastener on the outer side; the second fastener is comprised of a hook-type fastener; the third fastener is comprised of a loop-type fastener; and the fourth fastener is comprised of a hook-type fastener.

8. A carrier device useful with a support belt having opposed end segments adjustably connectable to each other with first fasteners, the belt also comprising a pair of tightening straps, each tightening strap having one end attached to the belt and an opposed end provided with a second fastener for adjustable connection to a respective one of the first fasteners, the carrier device comprising a body portion and a carrier section to carry a personal article of the wearer of the support belt, the body portion having a front face and a rear face, the front face having a third fastener for removable connection to the second fasteners and the rear face having a fourth fastener substantially directly opposite the third fastener for removable connection to the first fasteners so that the carrier device can be attached to both (i) one of the support belt end segments and (ii) one of the tightening straps so that the support belt can be adjusted without disengaging the carrier device from the support belt; wherein the carrier section comprises a pocket-forming cover having a plurality of edges, at least one of the edges being fastened to at least one of the faces of the body portion to form a cavity with an opening so that a personal article of the wearer of the belt can be inserted into the cavity.

9. The system of claim 8, wherein the first fasteners are comprised of a hook-type fastener on the inner side, and a loop-type fastener on the outer side; the second fastener is comprised of a hook-type fastener; the third fastener is comprised of a loop-type fastener; and the fourth fastener is comprised of a hook-type fastener.

10. A carrier device useful with a support belt having opposed end segments adjustably connectable to each other with first fasteners, the belt also comprising a pair of tightening straps, each tightening strap having one end attached to the belt and an opposed end provided with a second fastener for adjustable connection to a respective one of the first fasteners, the carrier device comprising a body portion and a carrier section to carry a personal article of the wearer of the support belt, the body portion having a front face and a rear face, the front face having a third fastener for removable connection to the second fasteners and the rear face having a fourth fastener substantially directly opposite the third fastener for removable connection to the first fasteners so that the carrier device can be attached to both (i) one of the support belt end segments and (ii) one of the tightening straps so that the support belt can be adjusted without disengaging the carrier device from the support belt; wherein the carrier section comprises a loop-forming material having two ends, each end of the loop-forming material is fastened to at least one of the faces of the body portion to form a loop so that a personal article of the wearer of the belt can be inserted into the loop, and thus carried by the carrier.

11. The carrier device of claim 10, wherein the loop-forming material is fastened to the body portion at multiple locations to form a plurality of loops so that a personal article of the wearer of the belt can be inserted into each loop, and thus carried by the carrier.

12. The system of claim 10, wherein the first fasteners are comprised of a hook-type fastener on the inner side, and a loop-type fastener on the outer side; the second fastener is comprised of a hook-type fastener: the third fastener is comprised of a loop-type fastener; and the fourth fastener is comprised of a hook-type fastener.

13. A carrier device useful with a support belt having opposed end segments adjustably connectable to each other with first fasteners, the belt also comprising a pair of tightening straps, each tightening strap having one end attached to the belt and an opposed end provided with a second fastener for adjustable connection to a respective one of the first fasteners, the carrier device comprising a body portion and a carrier section to carry a personal article of the wearer of the support belt, the body portion having a front lace and a rear face, the front face having a third fastener for removable connection to the second fasteners and the rear face having a fourth fastener substantially directly opposite the third fastener for removable connection to the first fasteners so that the carrier device can be attached to both (i) one of the support belt end segments and (ii) one of the tightening straps so that the support belt can be adjusted without disengaging the carrier device from the support belt; wherein the carrier device further comprises a tool-holding clip attached to at least one of the faces of the body portion so that a personal article of the wearer of the belt can be held within the tool-holding clip, and thus carrier by the carrier.

14. The system of claim 13, wherein the first fasteners are comprised of a hook-type fastener on the inner side, and a loop-type fastener on the outer side; the second fastener is comprised of a hook-type fastener: the third fastener is comprised of a loop-type fastener: and the fourth fastener is comprised of a hook-type fastener.

15. A carrier device useful with a support belt having opposed end segments adjustably connectable to each other with first fasteners, the belt also comprising a pair of tightening straps, each tightening strap having one end attached to the belt and an opposed end provided with a second fastener for adjustable connection to a respective one of the first fasteners, the carrier device compromising a body portion and a carrier section to carry a personal article of the wearer of the support belt, the body portion having a front face and a rear face, the front face having a third fastener for removable connection to the second fasteners and the rear face having a fourth fastener substantially directly opposite the third fastener for removable connection to the first fasteners so that the carrier device can be attached to both (i) one of the support belt end segments and (ii) one of the tightening straps so that the support belt can be adjusted without disengaging the carrier device from the support belt; wherein the carrier device further comprises a tool-holding rod attached to at least one of the faces of the body portion so that a personal article of the wearer of the belt can be carried by the tool-holding rod, and thus carried by the carrier.

16. The system of claim 15, wherein the first fasteners are comprised of a hook-type fastener on the inner side, and a loop-type fastener on the outer side; the second fastener is comprised of a hook-type fastener; the third fastener is comprised of a loop-type fastener: and the fourth fastener is comprised of a hook-type fastener.

* * * * *